United States Patent [19]

Davis

[11] Patent Number: 5,263,478
[45] Date of Patent: Nov. 23, 1993

[54] ENDOTRACHEAL TUBE INSERTION AND POSITIONING APPARATUS

[75] Inventor: Richard C. Davis, Palm Harbor, Fla.

[73] Assignee: Ballard Medical Products, Draper, Utah

[21] Appl. No.: 943,279

[22] Filed: Sep. 9, 1992

Related U.S. Application Data

[63] Continuation of Ser. No. 697,772, May 9, 1991, abandoned.

[51] Int. Cl.$^5$ .................... A61M 16/00; A62B 9/06
[52] U.S. Cl. ................. 128/207.14; 128/200.26; 128/207.17; 128/912; 604/96
[58] Field of Search ............. 128/200.26, 207.14, 128/207.15, 911, 912, DIG. 26, 207.17; 604/94, 96, 164, 165, 158, 117; 606/159, 192, 206

[56] References Cited

U.S. PATENT DOCUMENTS

| | | | |
|---|---|---|---|
| 3,516,408 | 6/1970 | Montanti | 604/96 |
| 3,538,918 | 11/1970 | Engelsher et al. | 128/200.26 |
| 3,760,811 | 9/1973 | Andrew | 128/207.17 |
| 3,799,173 | 3/1974 | Kamen | 128/207.15 |
| 4,256,099 | 3/1981 | Dryden | 128/200.26 |
| 4,273,128 | 6/1981 | Lary | 606/159 |
| 4,416,273 | 11/1983 | Grimes | 128/207.16 |
| 4,447,227 | 5/1984 | Kotsanis | 604/96 |
| 4,449,522 | 5/1984 | Baum | 128/200.26 |
| 4,453,545 | 6/1984 | Inoue | 128/207.15 |
| 4,646,733 | 3/1987 | Stroh et al. | 128/207.14 |
| 4,712,551 | 12/1987 | Rayhanabad | 604/96 |
| 4,787,399 | 11/1988 | Bonello et al. | 128/772 |
| 4,819,664 | 4/1989 | Nazari | 128/207.15 |
| 4,827,925 | 5/1989 | Vilasi | 128/207.14 |
| 4,840,172 | 6/1989 | Augustine et al. | 128/207.14 |
| 4,848,331 | 7/1989 | Northway-Meyer | 128/200.26 |
| 4,896,667 | 1/1990 | Magnuson et al. | 128/207.14 |
| 4,995,878 | 2/1991 | Rai | 604/96 |
| 5,003,963 | 4/1991 | Bullard et al. | 128/200.26 |
| 5,009,227 | 4/1991 | Njeuwstad | 128/200.26 |

FOREIGN PATENT DOCUMENTS

| | | | |
|---|---|---|---|
| 0812296 | 3/1981 | U.S.S.R. | 128/207.14 |
| 1024092 | 6/1983 | U.S.S.R. | 128/207.15 |
| 1303646 | 1/1973 | United Kingdom | 128/207.14 |

*Primary Examiner*—Edgar S. Burr
*Assistant Examiner*—Kimberly L. Asher
*Attorney, Agent, or Firm*—Lynn G. Foster

[57] ABSTRACT

An endotracheal tube apparatus (28) includes an elongated stylette (32) having a V-shaped distal end (58) and tube adaptor collar (30) for holding the stylette in a position in an endotracheal tube (10) in which the V-shaped distal end is in a first position near a distal end (16) of the endotracheal tube, but not extending substantially outside thereof, and for allowing the stylette to be moved longitudinally to a second position where the V-shaped distal end extends from the distal end of the endotracheal tube a fixed distance. Prongs (60, 62) of the V-shaped distal end have enlarged nodes which are as large as possible but yet which can be moved longitudinally within the endotracheal tube for removal of the stylette therefrom. The nodes include nesting side surfaces (68, 70) whereby a maximum cross sectional dimension of nested nodes is not substantially greater than a maximum cross sectional dimension of a single node. A retainer mouthpiece (104) locks the endotracheal tube in position at a patient's mouth while covering the mouth but allowing mouth care of the patient.

24 Claims, 4 Drawing Sheets

ENDOTRACHEAL TUBE INSERTION AND POSITIONING APPARATUS

This application is a continuation of co-pending U.S. patent application Ser. No. 07/697,772, filed May 9, 1991, now abandoned.

BACKGROUND OF THE INVENTION

This invention relates generally to the art of endotracheal tubes, and devices for facilitating implantation thereof.

Endotracheal intubation is a common medical procedure with over 55 million endotracheal (ET) tubes being sold annually. ET tubes are used in many situations for providing artificial airways for passages of respiratory gases to patients. ET tubes are used in both human and animal surgery to provide passageways for anaesthetic gases into lungs. They are used in emergency, life-threatening situations where patients have ceased spontaneous breathing (cardiac arrest, respiratory distress/arrest, seizures, and the like), thereby providing conduits for airway life support.

Normally ET tubes are flimsy plastic tubes which are difficult to manipulate. Thus, a more rigid malleable stylette is often placed into a central lumen of an ET tube for allowing an operator to better control the tube as it is implanted. That is, this added stiffness allows an operator to more easily manipulate a distal end of the ET tube between vocal cords and into a patient's trachea. Typically, such stylettes are firm, malleable rods made of metal and/or plastic. Normally, the stylette, or rod, is inserted the length of an ET tube's central lumen to a point just within a distal end thereof and then the ET tube is inserted into the trachea. In this regard, if such a firm-rod stylette were to extend beyond the distal end of the ET tube during insertion, its hard tip could potentially damage the vocal cords or other fine structures of a trachea, possibly even puncturing a hole through a trachea sidewall, or even through an esophagus sidewall, if mistakenly inserted thereinto.

To insert an ET tube into a patient, while he lies recumbent on his back, his neck is extended with his head tilted back. An operator, using his left hand to hold a laryngoscope, lifts the patient's tongue anteriorly, out of the way, thereby providing a line-of-sight, into a deepest portion of the patient's throat. This line-of-sight extends into the patient's esophagus. The esophagus is a large, wide, funnel-shaped structure. At an acute angle to the esophagus are an epiglottis and the patient's vocal cords, which define an entrance into the patient's trachea. Thus, an operator cannot actually view the trachea into which he is attempting to insert the ET tube.

In any event, with a stylette in the ET tube, the operator attempts to pass the ET tube between the vocal cords and into the trachea. However, due to the acuteness of the angle, poor lighting, poor visualization, and/or technical reasons, the ET tube may slide off the vocal cords and pass inadvertently into the esophagus. Should this occur, and not be recognized quickly, an unconscious patient will suffocate and die. This is a major problem in emergency situations and has multiple malpractice ramifications as well. Thus, it is an object of this invention to provide an endotracheal tube stylette apparatus which enables an operator to quickly and easily determine if an ET tube is mistakenly in an esophagus or is properly positioned in a trachea.

However, placement into a proper lumen (trachea rather than esophagus) at an appropriate depth is just a first technical hurdle to be overcome when properly implanting an ET tube. Assuming that an ET tube is properly inserted into a trachea, it is then incumbent on an operator to properly position the ET tube along the trachea. In this regard, the trachea is a relatively short tube, only 10-12 centimeters in length, and can be variable from one patient to another. The trachea divides into two distinct lumens at a carina, which is basically a bifurcation of the trachea. One of these lumens, a left mainstem bronchus, typically takes off at a very acute, nearly 90°, angle from the trachea, whereas the other, a right mainstem bronchus, takes off at a much shallower, oblique angle to the trachea. This anatomic fact is relatively constant. For this reason, if an ET tube is pushed too far into the trachea, it will inevitably track into the right main stem bronchus. This common complication of ET tube placement is called "endobronchial intubation". Should endobronchial intubation occur and should a retaining cuff of a standard ET tube be inflated in the right mainstem bronchus, this effectively seals the ET tube to the right lung only. This situation poses several mechanisms which produce potentially life-threatening problems for a patient. Firstly, if only the right lung is intubated, a left lung will not be ventilated or oxygenated. Therefore, efficacy of the entire procedure is reduced by 50%. Furthermore, since the operator does not realize he is operating in only one lung, he generates tidal volumes large enough for both lungs, all of which are forced into only the right lung. This presents the possibility of over-expansion and pneumothorax (explosive sudden collapse of a lung) of the right lung. This can rapidly cause compression of a heart leading to death by cardiac tamponade. Secondly, even in the absence of right lung collapse, the left lung will slowly collapse as stagnant gas is absorbed. This will eventually lead to a shift of the mediastinal structures and again, could lead to death by cardiac tamponade. For these reasons, it is another object of this invention to provide an endotracheal tube stylette apparatus which facilitates an operator determining when the endotracheal tube is in a proper position in the trachea, proximal to a carina. In this regard, it is a specific object of this invention to provide an endotracheal tube stylette apparatus with which an operator can space a distal end of an endotracheal tube a set distance from a patient's carina. Apparatus are described in Augustine et al U.S. Pat. No. 4,840,172 and Baum U.S. Pat. No. 4,449,522 for positioning distal ends of ET tubes anteriorally, or distally, of patients' carinas, however, the devices of these patents appear to be somewhat difficult to use in that they appear to require two hands, one hand to maneuver a positioning device and another hand to maneuver an endotracheal tube. Therefore, it is an object of this invention to provide an endotracheal tube stylette apparatus which allows an operator to properly position a distal end of an ET tube relative to a carina with one hand, that is, while maneuvering both the stylette apparatus and the ET tube with one hand.

Yet another difficulty with some positioning devices described in the prior art is that they do not allow tactile determination of fixed spacings of distal ends of ET tubes relative to carinas, but rather rely on operators determining proper positioning using sight. Such determinations are unduly complicated and require undue amounts of hand/eye coordination during emergency situations. Thus, it is another object of this invention to provide an endotracheal tube stylette apparatus with which an operator can mount an endotracheal tube in a patient with a distal end thereof properly positioned relative to a carina using touch alone.

Yet another problem with some prior art positioning devices is that they have distal tips which can damage throats, trachea, esophagi, epiglottises, and vocal cords by unduly scraping and gouging them. Therefore, it is another object of this invention to provide an endotracheal tube stylette apparatus which cannot unduly damage sensitive walls and organs of a throat, trachea, esophagus, epiglottis, or vocal cords.

It is another object of this invention to provide an endotracheal tube stylette apparatus which is uncomplicated in structure and which is therefore relatively inexpensive to construct.

Yet another object of this invention is to provide an endotracheal tube stylette apparatus which is relatively easy to use.

Another difficulty with some prior art endotracheal tube systems is that once they have been properly positioned, and their retaining cuffs have been inflated, proximal ends thereof are free to move laterally and longitudinally in patients' mouths. Further, with most prior art endotracheal tube systems patients can bite into cuff inflation tubes as well as into endotracheal tubes themselves. Also, with most prior art endotracheal tube systems, since patients' mouths must be maintained open during use thereof, debris, bacteria and the like can enter the mouths of the patients. Still further, prior art ET tubes are usually free to be pulled or pushed longitudinally so that their retaining cuffs can be moved in tracheas, thereby possibly damaging the tracheas and/or moving the ET tube to new undesirable positions. For these reasons, it is an object of this invention to provide an ET tube system including a retainer mouthpiece for aiding in holding an implanted ET tube at a proper lateral and longitudinal location, the retainer mouthpiece covering a patient's mouth, preventing the patient from biting portions of the ET tube, but yet allowing mouth care.

SUMMARY

According to principles of this invention, an endotracheal tube stylette apparatus comprises an elongated stylette having a V-shaped distal end with enlarged nodes at ends of prongs thereof and a tube adaptor collar for mounting the stylette on an endotracheal tube. The adaptor collar includes a stylette engaging device for holding the stylette in a position in which the V-shaped distal end thereof is near a distal end of the endotracheal tube but yet does not substantially extend outside thereof and for allowing the stylette to be moved longitudinally in said endotracheal tube to a second position where the V-shaped distal end extends from the distal end of said endotracheal tube a fixed distance. In one embodiment the stylette-engaging device comprises a spring for holding the stylette in the first position while allowing movement thereof to the second position. A stop on the tube adaptor collar defines the second position. The stylette includes a button on a proximal end thereof with an indicia thereon allowing an operator to determine orientation of the V-shaped distal end.

Each of the nodes on the prongs of the V-shaped distal end is substantially as large as possible while yet allowing longitudinal movement of the stylette in the endotracheal tube for removal of the stylette therefrom. The nodes have nesting side surfaces which are shaped to allow them to nest together so that a maximum cross section dimension of nested nodes is not substantially greater than a maximum cross sectional dimension of a single node.

A retainer mouthpiece having clip retainers for insertion into a retainer housing locks the endotracheal tube in position at a patient's mouth while covering the mouth but allowing mouth care of the patient.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1:
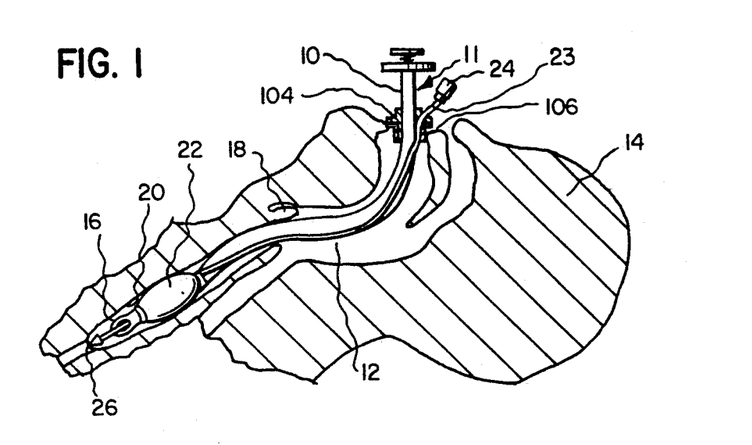
FIG. 1 is a segmented, partially cross sectional view of a patient with his head leaning back having an ET tube extending through his mouth into his trachea with an endotracheal tube stylette apparatus of this invention being used therewith.

Looking at FIG. 1, an endotracheal (ET) tube 10 of an endotracheal-tube system 11 extends into a throat 12 of a patient 14 with a distal end 16 thereof extending past an epiglottis and vocal cords (not shown) into the patient's trachea 20. The ET tube 10 includes an inflatable cuff 22 which is inflated via an inflation tube 23 attached to a check, one-way, valve 24 to expand against a wall of the trachea 20 to hold the ET tube 10 in place therein, with its distal end 16 spaced an appropriate distance from the patient's carina 26. A retainer mouthpiece 104 aids in holding the ET tube 10 in a proper position.

Figures 2, 3:
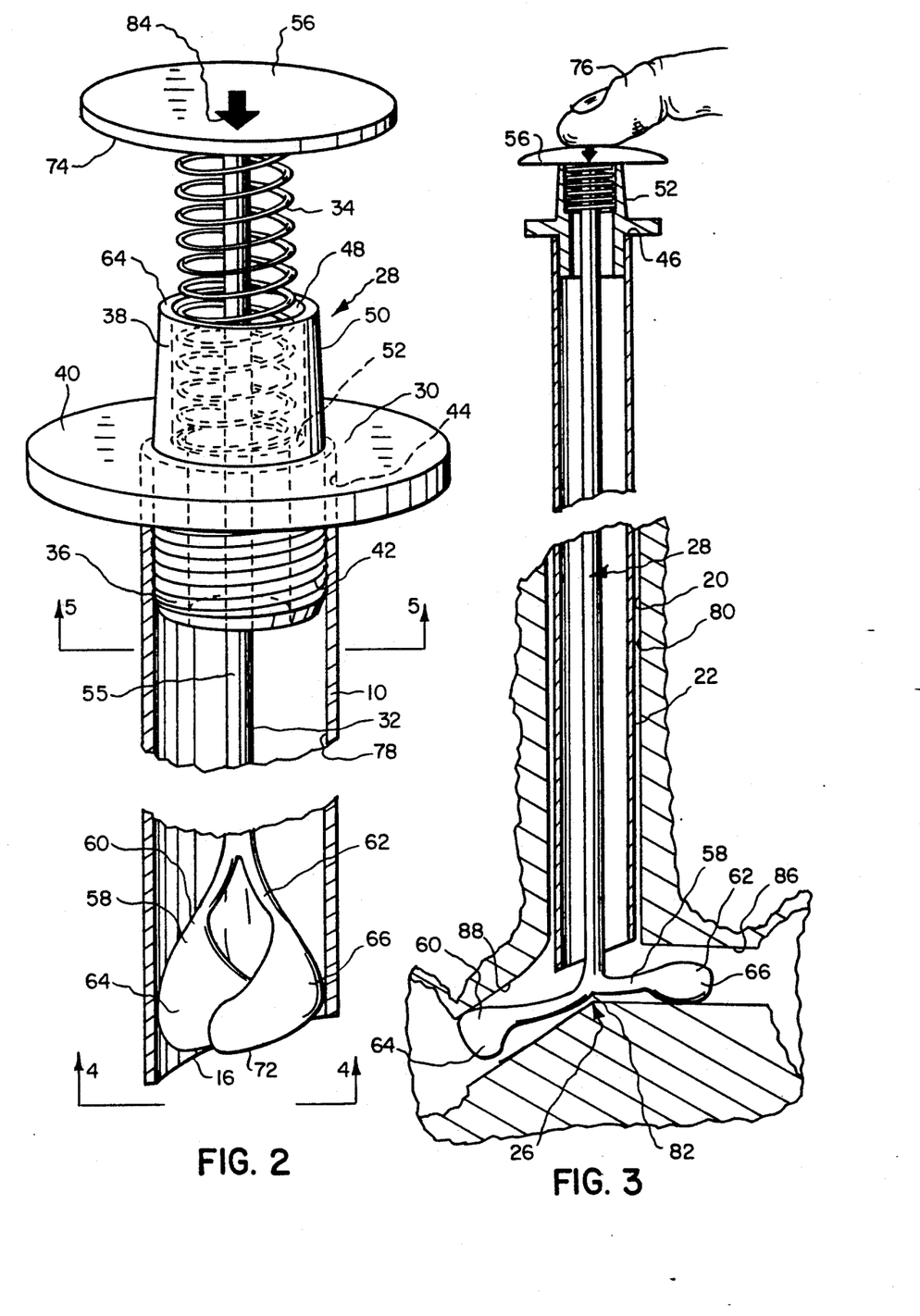
FIG. 2 is an isometric view, partially sectional, partially cutaway, of an endotracheal tube stylette apparatus of this invention mounted in an ET tube.
FIG. 3 is a front, partially sectional, segmented, view of an ET tube, having an endotracheal tube stylette apparatus of this invention used therewith, positioned in a trachea and right and left mainstem bronchi.
Figure 4:
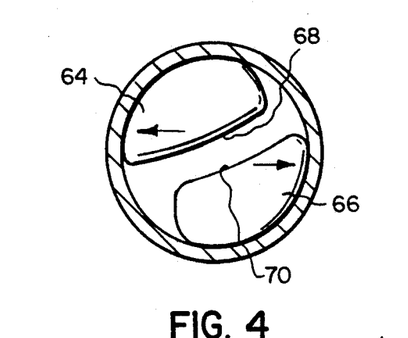
FIG. 4 is an end view of the endotracheal tube and stylette apparatus of FIG. 2 taken on line 4—4 of FIG. 2.

With regard to properly positioning the distal end 16 of the ET tube 10, one embodiment of an endotracheal tube stylette apparatus 28 of the endotracheal tube system 11 is shown in more detail in FIG. 2 mounted in the ET tube 10. The endotracheal tube stylette apparatus 28 includes a tube adaptor collar 30, a stylette 32, and a compression spring 34.

The tube adaptor collar 30 is molded of a hard resinous plastic to include a hollow mounting stub 36, a hollow spring retainer/stop 38, and a collar buttress 40. The mounting stub 36 is tubularly shaped with adaptor threads 42, or ridges, on an outer surface thereof and defining a collar bore 44. The adaptor threads 42 are of an appropriate size for being screwed, or shoved, into a proximate end 46 of the ET tube 10 so as to tightly mount the tube adaptor collar 30 thereto. A stylette shaft 55 passes through the collar bore 44 with a great deal of space therebetween.

The spring retainer/stop 38 is also circular and tubular in shape, defining a circular adaptor-spring seat recess 48 which is coaxial with, and which communicates with, the collar bore 44, although it has a greater diameter than the collar bore 44. The collar buttress 40 is a disc-shaped flange extending outwardly from the adaptor threads 42 and a standardly-tapered outer surface 50 of the spring retainer/stop 38 and is positioned at a transition between the collar bore 44 and the adaptor-spring seat recess 48, with the collar bore 44 extending therethrough to communicate with the adaptor-spring seat recess 48. In this regard, since the collar-bore 44 has a smaller diameter than the adaptor-spring seat recess 48, an adaptor-spring seat 52 is formed at a base of the spring retainer/stop 38 to serve as a partial floor for the adaptor-spring seat recess 48. A lower end of the compression spring 34 is received in the adaptor-spring seat recess 48 and impinges on the adaptor-spring seat 52, while an upper end extends upwardly well beyond a rim stop surface 54 of the spring retainer/stop 38 to a thumb button 56.

The stylette shaft 55 of the stylette 32 is constructed of a moldable, firm, rigid material to have a length for extending through the ET tube 10, the tube adaptor collar 30, and the compression spring 34 with the thumb button 56 being attached to a distal end of the stylette shaft 55 and impinging on an outer end of the compression spring 34.

Figure 5:
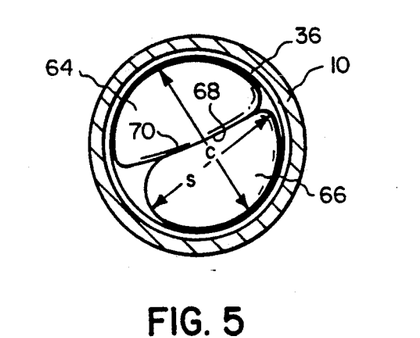
FIG. 5 is a cross sectional view taken on line 5—5 in FIG. 2 but with the endotracheal tube stylette apparatus thereof being partially pulled out of the ET tube and an attached tube adaptor collar so that nodes at ends of V-shaped prongs are positioned in a collar bore.

The distal end 58 of the stylette shaft 55 is basically V-shaped with a right prong 60 and left prong 62 of the V-shape having enlarged nodes 64 and 66 at the ends thereof. Unimpeded, the right and left prongs 60 and 62 are pre-biased to spring outwardly away from a main axis of elongation of the stylette shaft 55 so as to extend at angles in a range of 120°–160° thereto. In one embodiment, the stylette shaft 55 and the right and left prongs 60 and 62 of the V-shaped distal end 58 are constructed of resinous plastic. The enlarged nodes 64 and 66 are substantially as large as is possible while still being removable through the collar bore 44. In this regard, the enlarged nodes 64 and 66 have nesting surfaces 68 and 70 facing one another which are shaped so as to nest together as depicted in FIG. 5 when they are being pulled through the collar bore 44. In this configuration, with the nodes 64 and 66 nested together, their combined maximum cross sectional dimension "C" is not substantially greater than a maximum cross sectional dimension "S" of either of the nodes.

The length of the stylette shaft 55, that is, extending from distal node ends 72 to a bottom surface 74 of the thumb button 56, is such that when the compression spring 32 is expanded as shown in FIG. 2, thereby impinging on the thumb button 56 to hold the stylette shaft 55 in a raised position in the ET tube 10, the distal node ends 72 are near the distal ET tube end 16, still inside the ET tube. However, when an operator's finger (thumb, for example) 76 depresses the thumb button 56 to compress the compression spring 34 so that the thumb button's bottom surface 74 contacts the rim stop surface 54 of the spring retainer/stop 38 the right and left prongs 60 and 62 are forced out of the distal ET tube end 16 and are thereby allowed to expand as is shown in FIG. 3.

Looking now at a preferred embodiment of this invention depicted in FIGS. 6–10, similar elements of this preferred embodiment are referred to with the same numbers given elements in the FIGS. 1–5 embodiment but where the elements differ from those in FIGS. 1–5 embodiment they are designated with a prime symbol.

In the FIGS. 6–10 embodiment, a tube adaptor collar 30' differs from the tube adaptor collar 30 in that a spring retainer stop 38' and a mounting stub 36' thereof are larger than a spring retainer stop 38 and a mounting stub 36 of the FIGS. 1–5 embodiment so that the mounting stub 36' receives the ET tube 10 therein rather than being inserted into the ET tube 10. In this manner, the tube adaptor collar 36' does not reduce a usable internal diameter of the ET tube 10 as does the mounting stub 36 of the FIGS. 1–5 embodiment. Also, a thumb button cap 56' of the FIG. 6 embodiment forms a hollow hood whose inside top surface is attached to an upper end of a stylette shaft 55'. Ramp latches 86 are positioned on interior side surfaces of the thumb button cap 56' such that they can easily slide over opposite collar buttresses 40'. In this regard, rather than being a single round collar buttress 40 as is depicted in FIG. 2, the opposite collar buttresses 40' only extend partially around the tube adaptor collar 30'. The thumb button cap 56' further comprises an integral leaver 88. After the thumb button cap 56' has been pressed downwardly so that the ramp latches 86 engage with the collar buttresses 40' one can press upwardly on the integral leaver 88 which will cause a lower end of the thumb button cap 56' to rotate laterally until the ramp latches 86 clear the collar buttresses 40' thereby allowing the compression spring 34 to urge the thumb button cap 56', and the attached stylette shaft 55', upwardly. In this regard, the internal cavity of the thumb button cap 56', is quite a bit larger than the spring retainer stop 38' tube adaptor collar 30' so that the bottom end of the thumb button cap 56' can be moved laterally about the spring retainer stop 38'.

Figure 6:
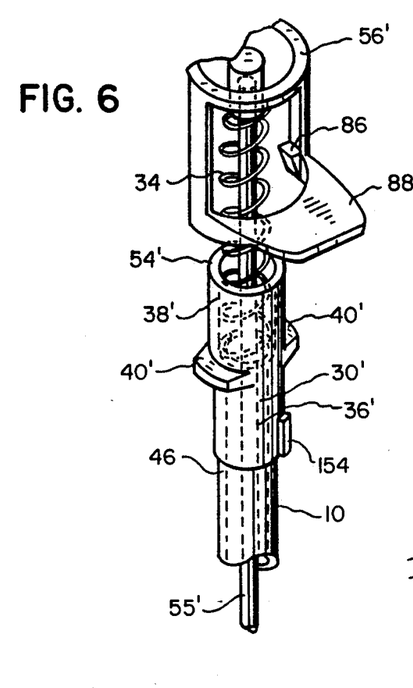
FIG. 6 is an isometric, partially cutaway, partially exploded, segmented view of a proximal end of a second embodiment endotracheal tube stylette system of this invention having a stylette mounted therein and including a second embodiment tube adaptor collar.
Figure 7:
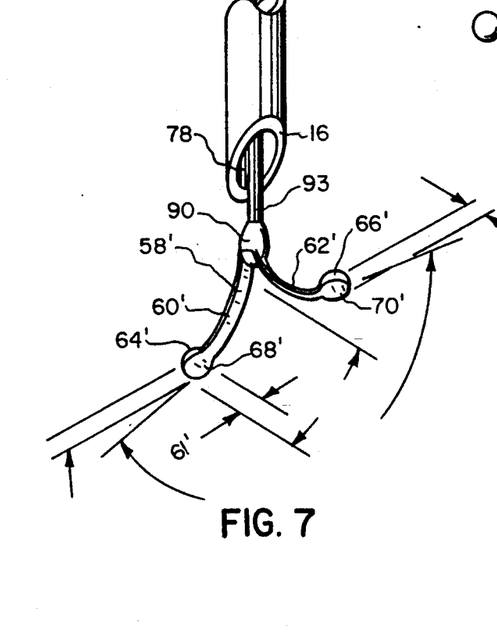
FIG. 7 is a isometric view of a distal end of the endotracheal tube stylette system of FIG. 6 when a thumb button thereof is depressed.
Figure 8:
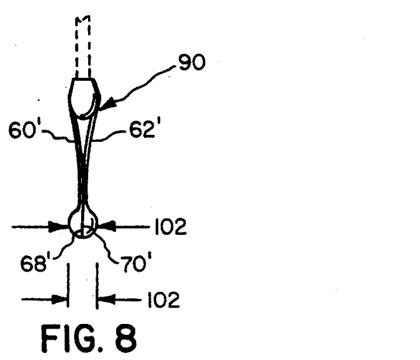
FIG. 8 is a side elevational view of a distal end of the stylette of the endotracheal tube stylette system of FIGS. 6 and 7 when an inward force is applied to prongs thereof.
Figure 9:
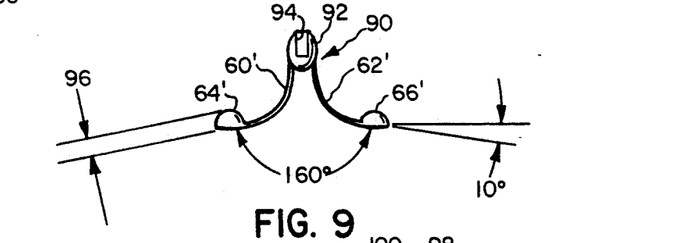
FIG. 9 is a side elevational view similar to FIG. 8 when no pressure is applied to the prongs thereof.
Figure 10:
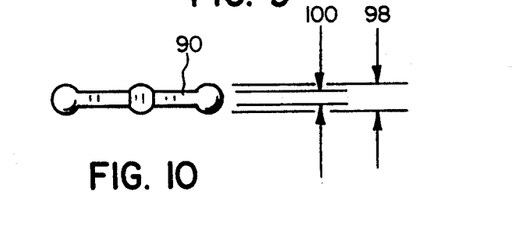
FIG. 10 is a bottom view of the distal end of the stylette prongs of FIG. 9.

In the preferred embodiment of FIGS. 6–10, the stylette shaft 55' is aluminum having a ⅛ inch diameter. In this embodiment, the stylette shaft 55' is separate from a plastic prong member 90 which is attached to a distal end 92 of the stylette shaft 55'. The prong member 90 is constructed of a resinous plastic material sold by General Electric under the trademark VALOX and comprises right and left prongs 60' and 62' and a hollow mounting receiver 92. The mounting receiver 92 includes a mounting cavity 94 therein for receiving a distal end 93 of the stylette shaft 55'. The right and left prongs 60' and 62' each respectively includes an enlarged node 64' or 66' at an outer end thereof. In this regard, in one embodiment each of these nodes has a thickness 96 of approximately 0.118 inches and a width 98 of approximately 0.236 inches. Their length along each of the right and left prongs 60' and 62' is approximately 0.188 inches as compared with the total length of each of the prongs being approximately one inch. The width 100 of the prongs away from the nodes is approximately 0.125 inches. When the prongs 60' and 62' are in an expanded configuration as depicted in FIGS. 7, 9 and 10, their outer ends extend away from one another at approximately 160°, with each extending at an angle of approximately 10° from a line perpendicular to the distal end 93 of the stylette shaft 55'. As can be seen in FIGS. 7–9 the thickness of the right and left prongs 60' and 62' away from the nodes 64 and 66 is quite thin. These prongs are prestressed to be in the expanded configuration of FIGS. 7, 9 and 10. But when a load is applied to force the nodes 64' and 66' toward one another, the right and left prongs 60' and 62' yield and nesting surfaces 68' and 70' of the nodes 64' and 66' come together as is depicted in FIG. 8. In this configuration, an approximate distance 102 across the two nodes is 0.236 inches, approximately the same as the width of each node.

Of course it must be kept in mind that these dimensions will change for different size endotracheal tube systems.

Looking next at a retainer mouthpiece 104 (FIG. 1) which surrounds the ET tube 10 at a mouth 106 of the patient 14, this member basically comprises a retainer housing 108 (FIG. 11), two clip retainers 110 and 112 and a bite guard 114. The retainer housing 108 is generally round in cross section forming a retainer-mouthpiece bore 116 therethrough for receiving and sliding along the ET tube 10. The retainer housing 108 includes a central, circular flange 118 with a cylinder wall 120 below the flange 118 being much thinner than a cylinder wall 122 located above the flange 118. Formed just above the flange 118 are lateral clip retainer cavities 123 and 124 for respectively receiving the clip retainers 110 and 112. On opposite portions of the flange 118 the flange enlarges to form downwardly-bent belt engagement extensions 125 and 126 having belt engagement openings and/or other devices 128 thereat and two mouth-care orifices 130 therein. In this respect, a belt, not shown, is engaged with the belt engagement openings and/or other devices 128 and extended about the head of the patient 14 for holding the retainer mouthpiece 104 at the patient's mouth 106. In this configuration, the belt-engagement devices 128 are positioned to the sides of the patient's mouth 106 while at least one of the mouth-care orifices 130 overlaps a side edge of the mouth 106. Thus, when the retainer mouthpiece 104 is held on the patient 14, suction and/or pressure tubes can be extended through the mouth-care orifices 130 for removing undesirable substances from the patient's mouth and/or introducing tubes and/or liquids into the mouth. In one embodiment, integral snap-covers 131 for the mouth-care orifices 130 are also included so that when pressure and suction tubes are not extended through the mouth-care orifices 130 the orifices can be closed off, thereby preventing extraneous matter from entering, or exiting the patient's mouth.

Figure 11:
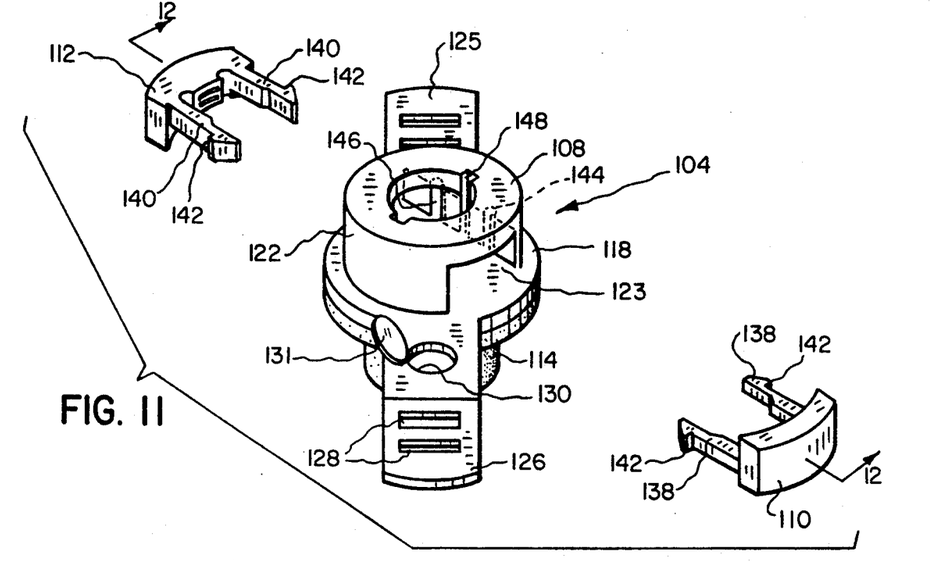
FIG. 11 is an exploded isometric view of a retainer mouthpiece of this invention which is part of the endotracheal tube system of FIG. 1.

The bite guard 114 is formed of a softer material than is the retainer housing 108 so as to protect soft surfaces of the patient's mouth and also to provide a relatively soft, but tough, material against which the patient can bite. An inner diameter 132 of the bite guard 114 is of a size to tightly fit an exterior surface 134 of the wall 120 so as to be tightly held thereon. In one embodiment, the bite guard 114 also includes a flange 136 covering a bottom surface of the flange 118. The bite guard 114 is formed of a soft flexible, tough, foam material in a preferred embodiment.

Figure 12:
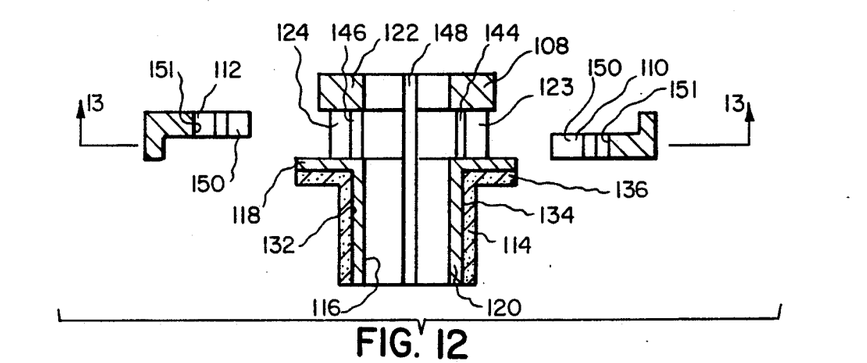
FIG. 12 is a side, cross sectional, view of a retainer mouthpiece taken on line 12—12 of FIG. 11.
Figure 13:
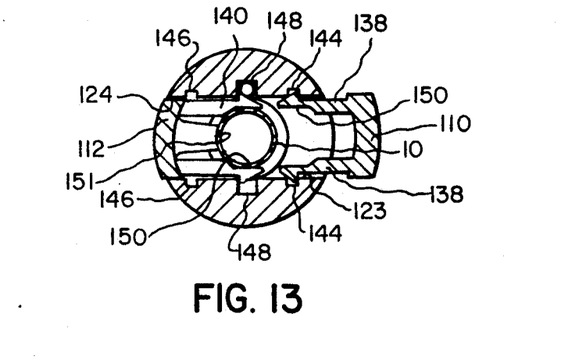
FIG. 13 is a top cross sectional view of a retainer mouthpiece taken on line 13—13 of FIG. 12 with clip retainers being inserted thereinto.

The clip retainers 110 and 112 are U-shaped, each including opposite spring legs 138 and 140 respectively with outwardly-directed latching feet 142 near the respective ends thereof. It should be noted that the spring legs 138 of clip retainer 110 are located at a bottom portion of the clip retainer 110 while the spring legs 140 of the clip retainer 112 are located at a top portion of the clip retainer 112. In this regard, these clip retainers 110 and 112 can actually be identical elements, with one being turned over. In any event, when these clip retainers 110 and 112 are inserted into their respective clip-retainer cavities 123 and 124 their respective latching feet 142 first engage holding notches 144 and 146 formed in the respective clip-retainer cavities 123 and 124 and then engage the locking notches 148. When it is desired to lock the retainer mouthpiece 104 onto an outer surface of the ET tube 10 the clip retainers 110 are pressed inwardly so that their latching feet 142 disengage from their respective holding notches 144 and 146 and reengage in the locking notches 148. In this locking configuration inner surfaces 150 and 151 of the clip retainer 110 and 112 engage an outer surface of the ET tube 10 thereby locking it in its longitudinal position. When this is done, it can be seen that the spring legs 138 of the clip retainer 110 overlap the spring legs 140 of the clip retainer 112, with the spring legs 138 being positioned below the spring legs 140. It would be possible to configure this device so that the spring legs of the tube clip retainers always overlap one another even when they are in holding positions engaged with the holding notches 144 and 146.

Figures 14, 15:
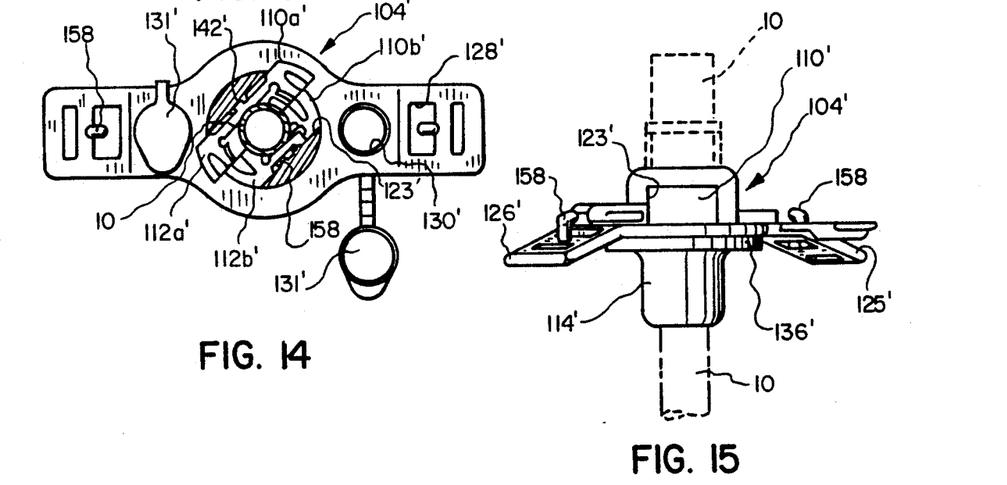
FIG. 14 is a cross sectional, partially cutaway, view of a second embodiment retainer mouthpiece with two opposite clip halves being schematically shown in inserted positions, and two opposite clip halves being shown in noninserted positions.
FIG. 15 is a side view of the second embodiment retainer mouthpiece of FIG. 14 locked on an endotracheal tube.

FIGS. 14 and 15 depict a second embodiment retainer mouthpiece 104' which is quite similar to the retainer mouthpiece of FIGS. 11–13. In this regard, the retainer mouthpiece 104' has protrusions 156 in its clip retainer cavity 123' (the elements of the second embodiment retainer mouthpiece 104' of FIGS. 14 and 15 are numbered similarly to those of the embodiment of FIGS. 11–13 but where the elements are slightly different, they are designated with prime symbols) to engage the latching feet 142' of the clip retainers 110' and 112'. In FIG. 14, the clips 110' and 112' are schematically depicted as being divided into two halves 110a', 110b' and 112a' and 112b'. The clip halves 110b' and 112b' are shown fully inserted and the clip halves 110a' and 112a' are shown not fully inserted. As shown in FIG. 15, hooks 158 are included on the belt-engaging extensions 125' and 126' to aid in engaging a belt (not shown).

Otherwise, the second embodiment retainer mouthpiece 104' of FIGS. 14 and 15 is constructed and operates substantially as the retainer mouthpiece 104 of FIGS. 11-13, and it should be understood that the reference numerals used in describing the embodiment of FIGS. 11-13 can also be used with the prime designations of FIGS. 14 and 15 to describe the second embodiment.

Describing now use of the endotracheal tube stylette apparatus of this invention, the patient 14 is positioned in the same manner as was done in the prior art. The endotracheal tube stylette apparatus 28 of this invention is sterile packaged with the stylette shaft 55 extending through the collar bore 44 and with a compression spring 34 in position as shown in FIG. 2. The ET tube extends through the retainer-mouthpiece bore 116 and the tube adaptor collar 30 is in engagement with an upper end of the retainer mouthpiece 104 and can be keyed thereto by a key 154 on the tube adaptor collar 30' (FIG. 6). In this respect, an operator can use the belt engagement extensions 125 and 126 of the retainer mouthpiece 104 to properly orient the ET tube 10 during insertion. The endotracheal tube stylette apparatus is removed from its sterile package with the tube adaptor collar 30 being attached to the proximate end portion 46 of the ET tube 10. (Again, reference numerals used in this description of operation not only refer to those elements designated by the numerals but to those elements designated by prime counterparts of the numerals as well.) An operator then bends the malleable stylette shaft 55 to have an appropriate shape for insertion of the ET tube 10 into the trachea 20 of the patient 14. The ET tube 10 has a curved configuration to fit a trachea and includes an X-ray opaque metallic strip material on a top rather than a bottom side thereof so that it provides better visual guidance during insertion. The operator then inserts the distal ET tube end 16 through the throat 12, past the epiglottis 18 and vocal cords (not shown), into the trachea 20. Once the operator can see that the distal ET tube end 16 has passed beyond the vocal cords he places a finger 76 onto the thumb button 56 and depresses it until it contacts the rim stop surface 54. In the FIG. 2 embodiment continuous thumb pressure is maintained to hold the button against the rim stop surface 54 of the tube adaptor collar 30; however, in the FIG. 6 embodiment the ramp latches 86 hold the button in a depressed condition. Depression of the thumb button 56 advances the V-shaped distal end 58 of the stylette shaft 55 beyond the distal ET tube end 16 a distance equal to the distance of travel of the thumb button 56 relative to the rim stop surface 54. As the right and left prongs 60 and 62 are now no longer contained in an ET tube bore 78, they spring laterally outwardly, pressing against a side wall 80 of the trachea. The rounded enlarged outer surfaces of the enlarged nodes 64 and 66 slide harmlessly down the mucosa lined trachea sidewall 80. At its fully depressed position, an apex, or base, 82 of the V-shaped distal end 58 is now positioned 2.5 centimeters, or around one inch, distal to the distal ET tube end 16.

Once the thumb button 56 has been depressed in this manner, and the enlarged nodes 64 and 66 extend out to the trachea sidewall 80, the entire apparatus, including the ET tube 10 and the extended stylette 32, are further advanced into the patient's trachea 20. A correct anterior/posterior positioning of the stylette shaft must be determined by the operator during this insertion process. In order to do this, the operator maintains an arrow indicia 84 on the thumb button 56 in a proper orientation so as to maintain the left and right prongs 60 and 62 of the V-shaped distal end 58 in a proper orientation. Other methods of maintaining proper orientation are also available. For example, the integral leaver 88 of the FIG. 6 embodiment can be used to provide proper orientation. In any event, when the enlarged nodes 64 and 66 arrive at left and right mainstem bronchi 86 and 88, they expand naturally thereinto and the apex or base 82 of the V-shaped distal end 58 eventually impinges on the carina 26 of the patient. That is, when the two laterally biased spring prong enlarged nodes 64 and 66 encounter the widening channel at the carina, each prong begins to expand further, tracing a path into each individual mainstem bronchus. The right prong expands into the right mainstem bronchus and the left prong into the left mainstem bronchus. Further advancing the ET tube 10 with the endotracheal tube stylette apparatus 28 wedges the base 82 of the distal V-shaped end 58 on the carina 26 and further advancement is impeded. Using only touch, the operator can easily feel this resistance to further advancement and knows that the distal tip 16 of the ET tube is now precisely 2.5 centimeters from the carina 26, which is a perfect placement. At this time, the operator notes the tube placement distance at an angle of the patient's mouth looking at distance marks on the ET tube 10. Further, the operator expands the inflatable cuff 22 to anchor the ET tube 10 in this position in the trachea. The retainer mouthpiece 104 is now separated from the tube adaptor collar 30 and moved downwardly along the ET tube 10 until the bite guard 114, which surrounds the wall 120 of the retainer mouthpiece 104 extends into the mouth 106 of the patient 14. A belt (not shown) is then attached to the belt-engagement extensions 125 and 126 and tied about the patient's head. The clip retainers 110 and 112 are pressed inwardly so that their latching feet 142 move into the locking notches 148, thereby permanently locking the retainer mouthpiece 104 on the ET tube 10. In this position, the clip retainers 110 and 112 impinge on the ET tube 10 and hold it firmly to the retainer mouthpiece 104, thereby further preventing movement of the ET tube. If for some reason the operator should need to have the retainer mouthpiece 104 at a different position relative to the ET tube 10, he must remove the ET tube and start over with a new ET tube apparatus. He cannot adjust the retainer mouthpiece 104 along the ET tube once it has been locked in position. The stylette 32 and the compression spring 34 are withdrawn with the right and left enlarged nodes 64 and 66 pressing together at their nesting surfaces 68 and 70 to pass through the ET tube bore 78 and the collar bore 44. In this regard, in the FIG. 6 embodiment the nodes 64' and 66' can be larger than can the nodes of the FIG. 2 embodiment because in the FIG. 6 embodiment the tube adaptor collar 30' does not restrict their removal through the ET tube bore 78. The tube adaptor collar 30 is then attached to a ventilation source as per standard methods.

It should be understood that in performing this procedure if the distal ET tube end 16 does not actually pass between the vocal cords and through the epiglottis into the trachea, but rather is inadvertently passed into the esophagus, the stylette 32 will never seat against the carina. Since there are no similar structures in a normal esophagus, the operator will continue to advance the apparatus unimpeded to the hilt of the tube adaptor collar 30. This will alert the operator to the fact that the ET tube is in the esophagus and will allow the operator to immediately reattempt proper ET tube placement without an undue time delay.

It will be appreciated by those of ordinary skill in the art that the device of this invention provides many features which facilitate proper placement of ET tubes. As ET tubes are manufactured in a gentle curve to allow easier placement, so to is the shaft of the stylette curved in an anterior/posterior plane. The distal V-shaped end is composed of a bifurcated V-shaped member having two prongs, with each prong of the V being rounded at its most distal end and being biased to flex outwardly, laterally and in a horizontal plain. By including enlarged nodes thereon which are substantially as large as possible, surfaces of the throat, trachea, and esophagus are protected from injury.

In a preferred embodiment, the right and left prongs are approximately 2.5 centimeters (1 inch) in length and are constructed of a material having a durometer such that the prongs are spring-like and biased toward lateral expansion. However, lateral tension of such bias pressure should not exceed 20 centimeters of water pressure. By limiting outward bias tension, a possibility of damaging a mucosal lining of a trachea or esophagus is minimized during tube placement.

In one embodiment the enlarged nodes are convex in three dimensions on their outer surfaces however inwardly they are substantially flat to allow them to nest together when compressed together. In one embodiment the nodes are six millimeters in their widest dimension and nest together to form a six millimeter by six millimeter ovoid shape. This shape precludes puncturing, penetrating, or otherwise damaging fine tracheal or esophageal structures.

It will be appreciated that with the endotracheal tube stylette apparatus of this invention an operator can accurately implant an ET tube with one hand.

The retainer mouthpiece of FIGS. 11-13 enables an operator to quickly and securely affix the position of an ET tube in a patient's mouth by locking it thereto with clip retainers. The retainer mouthpiece 104 also protects from patients' teeth not only the endotracheal tube 10 but also the inflation tube 23 which can extend on the inside of the retainer mouthpiece 104 through one of the locking notches 148. A separate notch could also be provided therefor.

Normally, medical personnel employ tape for holding ET tubes in position on a person's mouth. Such tape is uncomfortable for a patient and is not particularly effective in holding an ET tube stationary while taping the tube into place. The retainer mouthpiece 104 is much more comfortable for a patient, can be quickly activated by an operator and is much more effective for holding an ET tube in a stationary position on a patient, especially during initial placement.

It will be appreciated by those of ordinary skill in the art that the tube adaptor collar 30' of FIG. 6, with its large female mounting stub 36' which receives the ET tube 10 therein provides many benefits over a male adaptor collar 30 as is shown in FIG. 2. Since the mounting stub 36' does not restrict flow through the ET tube, patient's who are being weaned from a respirator need not be forced to create greater pressure for exhaling. Also, flow of air and insertion of tools through the ET tube is enhanced. Also, the nodes 64' and 66' can be larger.

It should be appreciated that the belt-engagement extensions 125 and 126 of the retainer mouthpiece 104 of FIG. 11 are extremely effective for keeping a mouth of a patient covered while yet providing mouth-care orifices for providing selective access to a patient's mouth.

While the invention has been particularly shown and described with reference to a preferred embodiment, it will be understood by those skilled in the art that various changes in form and detail may be made therein without departing from the spirit and scope of the invention. For example, the stylette could include a foam pad at the apex, or base, so as to protect the carina. Also, the V-shaped distal end of the stylette could include three prongs, thereby forming three V's, in which case the stylette would be less orientation sensitive. Also, the compression spring could be a separate member, or it could be attached to the thumb button and/or directly to the stylette shaft.

The retainer housing 108 of the retainer mouthpiece 104 can be made sufficiently large to fit various sizes of ET tubes while the inner surfaces 150 and 152 of the clip retainers 110 and 112 can be of various sizes to fit the various sizes of ET tubes.

The embodiments of the invention in which an exclusive property or privilege are claimed or defined are as follows:

I claim:

1. A stylette apparatus used to aid insertion of an endotracheal tube past an epiglottis of a patient and to further position the endotracheal tube at a predetermined position relative to the carina of the patient, said tube comprising a proximal end and a distal end, said apparatus comprising:

stylette means comprising exterior peripheral dimensions which fit for slidable movement within a bore of the endotracheal tube; a length which is longer by a predetermined distance than the endotracheal tube, a proximally disposed shaft end, and a distally disposed bifurcated end comprising a pair of prongs which are self-biased to spread apart at a sensible bifurcation site when not otherwise contained;

adapter means interposed between the proximal ends of the stylette and the endotracheal tube, said adapter means comprising an endotracheal tube connector whereby the proximal end of the endotracheal tube is firmly attached at a predetermined location relative to the adapter means, a digitally operated stylette actuator comprising memory means by which the actuator is proximally biased away from the proximal end of the endotracheal tube at a first position, a stylette connector for connecting the proximal end of the stylette to the actuator such that the stylette and endotracheal tube are initially inserted past the epiglottis of a patient while the actuator is biased by said memory means in the first position and, after such insertion, the stylette is moved distally against the bias of the memory means through the endotracheal tube by action of a single digit of a hand moving the actuator and therefore the stylette to a second position relative to the endotracheal tube whereat said prongs seperate and said sensible bifurcation site is a predetermined distance from the distal end of said endotracheal tube.

2. The stylette apparatus according to claim 1 wherein each of said prongs comprise large vessel following nodes having a transverse width of approximately the same dimension as the inner diameter of the endotracheal tube.

3. The stylette apparatus according to claim 1 wherein the endotracheal tube connector comprises a female connector to provide a through pathway through the endotracheal tube and the stylette apparatus which is no smaller than the internal bore of the endotracheal tube.

4. The stylette apparatus according to claim 1 wherein the shaft comprises a portion which is malleable such that the shaft is formable to meet individual patient insertion requirements.

5. The stylette apparatus according to claim 1 wherein said shaft comprises a portion formed to an appropriate shape for concurrent endotracheal tube supportive insertion of the endotracheal tube into a trachea of a patient by said stylette means while the stylette means are disposed in the first position.

6. The stylette apparatus according to claim 1 wherein the actuator comprises a lock which retains the stylette in the second position upon movement to the second position.

7. The stylette apparatus according to claim 1 wherein the actuator memory means comprises a spring which holds the stylette in said first position but flexes under pressure of the single digit to permit the actuator to be moved to said second position.

8. The stylette apparatus according to claim 1 wherein the actuator comprises a stop which limits movement at said second position.

9. The stylette apparatus according to claim 1 wherein said actuator comprise a button at a proximal end of said stylette apparatus.

10. The stylette apparatus according to claim 9 wherein said button comprises an indicia means thereon for indicating to an operator the orientation of the bifurcated end.

11. The stylette apparatus according to claim 1 wherein said stylette apparatus comprises means for fully removing said stylette means and actuator means from said endotracheal tube and stylette apparatus.

12. Apparatus associated with aiding insertion of an endotracheal tube past an epiglottis of a patient, to further position the endotracheal tube at a predetermined position relative to the carina of the patient, said tube comprising a proximal end and a distal end, and retain the endotracheal tube at the predetermined position relative to the carina, said apparatus comprising:

a stylette apparatus comprising:
stylette means comprising exterior peripheral dimensions which fit for slidable movement within a bore of the endotracheal tube, a length which is longer by a predetermined distance than the endotracheal tube, a proximally disposed shaft end, and a distally disposed bifurcated end comprising a pair of prongs which are self-biased to spread apart at a sensible bifurcation site when not otherwise contained;
adapter means interposed between the proximal ends of the stylette and the endotracheal tube, said adapter means comprising an endotracheal tube connector for firmly attaching the proximal end of the endotracheal tube at a predetermined location relative to the adapter means, a digitally operated stylette actuator comprising memory means by which the actuator is proximally biased away from the proximal end of the endotracheal tube at a first position, a stylette connector for connecting the proximal end of the stylette to the actuator such that the stylette and endotracheal tube are initially inserted past the epiglottis of a patient while the actuator is biased by said memory means in the first position and, after such insertion, the actuator having a second position wherein the stylette is moved distally against the bias of the memory means through the endotracheal tube by action of a single digit of a hand moving the actuator and therefore the stylette to said second position relative to the endotracheal tube whereat said prongs separate and said sensible bifurcation site is a predetermined distance from the distal end of said endotracheal tube;

an endotracheal tube retainer and mouth cover surrounding the endotracheal tube and comprising means for selectively and rigidly affixing the retainer and mouth cover to an outer surface of the endotracheal tube.

13. The apparatus according to claim 12 wherein said retainer and mouth cover comprises a retainer housing made from a relatively hard material and a bite guard attached to the retainer housing for extending into the mouth of a patient.

14. The apparatus according to claim 12 wherein said retainer and mouth cover comprises at least one flange extension for covering a portion of the mouth of the patient, said at least one flange extension having a mouth care opening and a removable cover therefor, access to the mouth of the patient being provided when the cover is removed.

15. The apparatus according to claim 12 wherein said retainer and mouth cover comprises head-attaching means for attaching the retainer to the head of the patient.

16. The apparatus according to claim 12 wherein said retainer and mouth cover comprises a separate bite guard of softer material than said retainer housing, said bite guard covering a portion of said retainer housing extending into the mouth of said patient.

17. The apparatus according to claim 12 wherein said retainer and cover affixing means comprise at least one clip retainer for affixing the endotracheal tube to the retainer and mouth cover.

18. The apparatus according to claim 17 wherein said clip retainer comprises locking means for permanently affixing said clip retainer in place once the clip retainer is disposed in an endotracheal tube retaining position.

19. A method for inserting an endotracheal tube past an epiglottis of a patient and to a predetermined position relative to the carina of the patient, comprising the steps of:

(a) releasibly affixing a stylette to an endotracheal tube with the stylette disposed in a first position relative to the endotracheal tube, the stylette comprising a pair of prongs;

(b) concurrently delivering the endotracheal tube and stylette past an epiglottis into a trachea of a patient;

(c) using a single hand, distally advancing the stylette relative to the endotracheal tube and releasing the pair of transversely outwardly self-separating prongs attached to the stylette;

(d) further advancing both the endotracheal tube and stylette distally using one hand only such that a distal end of each prong follow a separate pathway of a main bronchus of the patient while testing for detectible advance retarding contact of a portion of said prongs against the patient's carina; and (e) when such advance retarding contact is sensed, affixing the endotracheal tube in place and removing the stylette from the endotracheal tube.

20. The method according to claim 19 wherein the distal advancing step is preceded by orienting said pair of transversely outwardly self-separating prongs to coincide with direction of bifurcation of the main bronchial pathways of the patient.

21. The method according to claim 20 wherein the stylette comprising visually accessing indicia and the orienting step comprises discerning the relative orientation of said prongs by the visually accessing indicia.

22. The method according to claim 19 wherein the stylette comprises a malleable shaft and the releasibly affixing step comprises shaping the malleable shaft of the stylette to provide supportive assistance to longitudinal curvature of the endotracheal tube for facilely delivering the endotracheal tube and stylette past the epiglottis.

23. The method according to claim 19 comprising the additional step of quickly removing the endotracheal tube and stylette from the patient to repeat the method when it is determined during the further advancing step that travel without detecting a carina of the endotracheal tube and stylette is greater than a predetermined distance to the carina and a decision is made that the endotracheal tube and stylette reside in the esophagus of the patient.

24. The method according to claim 19 wherein steps (c) through (f) comprise manipulating the endotracheal tube and stylette with a single hand.

* * * * *